United States Patent
La Lumondiere et al.

(10) Patent No.: US 8,461,532 B2
(45) Date of Patent: Jun. 11, 2013

(54) REFRACTION ASSISTED ILLUMINATION FOR IMAGING

(75) Inventors: Stephen La Lumondiere, Torrance, CA (US); Terence Yeoh, Pasadena, CA (US); Martin Siu Wo Leung, Redondo Beach, CA (US); Neil A. Ives, Hawthrone, CA (US)

(73) Assignee: The Aerospace Corporation, El Segundo, CA (US)

( * ) Notice: Subject to any disclaimer, the term of this patent is extended or adjusted under 35 U.S.C. 154(b) by 433 days.

(21) Appl. No.: 12/661,967

(22) Filed: Mar. 26, 2010

(65) Prior Publication Data

US 2011/0102615 A1   May 5, 2011

Related U.S. Application Data

(63) Continuation-in-part of application No. 12/590,292, filed on Nov. 5, 2009, now Pat. No. 8,138,476.

(51) Int. Cl.
*G01J 5/02* (2006.01)

(52) U.S. Cl.
USPC ................................................ 250/339.11

(58) Field of Classification Search
USPC ........................................ 250/339.01–339.15
See application file for complete search history.

(56) References Cited

U.S. PATENT DOCUMENTS

| | | | |
|---|---|---|---|
| 5,131,963 A | 7/1992 | Ravi | |
| 5,192,980 A | 3/1993 | Dixon et al. | |
| 5,196,716 A | 3/1993 | Moriya et al. | |
| 5,220,403 A | 6/1993 | Batchelder et al. | |
| 5,754,514 A | 5/1998 | Guerra | |
| 5,757,050 A | 5/1998 | Adler et al. | |

(Continued)

FOREIGN PATENT DOCUMENTS

| | | |
|---|---|---|
| EP | 0887621 A1 | 12/1998 |
| WO | WO 98/21687 | 5/1998 |
| WO | WO 2008/119550 A1 | 10/2008 |
| WO | WO 2008/120883 A1 | 10/2008 |

OTHER PUBLICATIONS

Vasefi et al., "An Optical Imaging Technique Using Deep Illumination in the Angular Domain," 2007, IEEE Journal of Selected Topics in Quantum Electronics, vol. 13, No. 6, pp. 1610-1620.
Office Action mailed Nov. 26, 2010 in U.S. Appl. No. 12/590,262.

(Continued)

*Primary Examiner* — Kiho Kim
(74) *Attorney, Agent, or Firm* — K & L Gates LLP

(57) ABSTRACT

An illumination source may be directed towards a surface of an object comprising subsurface features, wherein the illumination from the source is directed at a first angle relative to the normal of the surface. The object may have a portion between the subsurface features and the surface, the portion having an index of refraction that is greater than the index of refraction of a surrounding medium that surrounds the object. An imaging device may be placed with an objective lens. The first angle may be larger than an acceptance angle of the objective lens. In some embodiments, multiple illumination beams may be generated by one or more illumination sources. The beams may be rotated relative to one another about the normal of the surface. Also, in some embodiments, multiple images may be taken with the objective of the imaging device at different positions rotated off of the normal. The multiple images may be combined to generate a composite image.

18 Claims, 12 Drawing Sheets

U.S. PATENT DOCUMENTS

| | | | |
|---|---|---|---|
| 5,900,354 A * | 5/1999 | Batchelder | 430/395 |
| 5,930,588 A | 7/1999 | Paniccia | |
| 5,946,543 A | 8/1999 | Kimura et al. | |
| 5,966,019 A | 10/1999 | Borden | |
| 6,005,965 A | 12/1999 | Tsuda et al. | |
| 6,055,055 A | 4/2000 | Toh | |
| 6,266,130 B1 | 7/2001 | Hasegawa et al. | |
| 6,731,660 B2 | 5/2004 | Arbore et al. | |
| 6,734,960 B1 | 5/2004 | Goto et al. | |
| 6,859,516 B2 | 2/2005 | Schneider et al. | |
| 6,906,801 B2 | 6/2005 | Borden et al. | |
| 7,890,158 B2 | 2/2011 | Rowe et al. | |
| 8,212,215 B2 | 7/2012 | La Lumondiere et al. | |
| 8,254,020 B2 | 8/2012 | Holy et al. | |
| 2002/0005493 A1 | 1/2002 | Reese et al. | |
| 2002/0180965 A1 | 12/2002 | Engelhardt et al. | |
| 2004/0119018 A1 | 6/2004 | Alfano et al. | |
| 2005/0001900 A1 | 1/2005 | Kreh et al. | |
| 2005/0231713 A1 | 10/2005 | Owen et al. | |
| 2005/0245005 A1 | 11/2005 | Benson | |
| 2007/0031995 A1 | 2/2007 | Kaneko | |
| 2008/0240548 A1 | 10/2008 | Yeoh et al. | |
| 2009/0002688 A1 | 1/2009 | Soeda et al. | |
| 2009/0045415 A1 | 2/2009 | Koshiba | |
| 2009/0066933 A1 | 3/2009 | Takano et al. | |
| 2011/0102770 A1 | 5/2011 | La Lumondiere et al. | |
| 2012/0019707 A1 | 1/2012 | La Lumondiere et al. | |

OTHER PUBLICATIONS

Office Action mailed Mar. 24, 2011 in U.S. Appl. No. 12/590,262.
International Search Report and Written Opinion of the International Search Authority mailed in Application No. PCT/US2011/028514 on Jun. 24, 2011.
ISR and Written Opinion of the International Search Authority mailed in Application No. PCT/US2010/046978 on Dec. 17, 2010.
Office Action mailed Jul. 27, 2011 in U.S. Appl. No. 12/590,262.
Notice of Allowance mailed Nov. 14, 2011 in U.S. Appl. No. 12/590,262.
Springholz, G., "Strain contrast in scanning tunneling microscopy imaging of subsurface feature dislocations in lattice-mismatched heteoepitaxy", 1997, Applied Surface Science, vol. 112, pp. 12-22.
Ramsay et al., "Three-dimensional nanometric sub-surface imaging of a silicon flip-chip using the two-photon optical beam induced current method", 2007, Microelectronics Reliability, vol. 47, pp. 1534-1538.
Pfister et al., "Surface and subsurface imaging of indium in InGaAs by scanning tunneling microscopy", 1996, Applied Surface Science, vol. 104/105, pp. 516-521.
Non-Final Office Action mailed Sep. 19, 2012 in U.S. Appl. No. 13/190,264.
Notice of Allowance mailed Mar. 20, 2012 in U.S. Appl. No. 13/368,026.

* cited by examiner

REFRACTION ASSISTED ILLUMINATION FOR IMAGING

PRIORITY CLAIM

This application is a continuation-in-part of co-pending U.S. application Ser. No. 12/590,262 filed on Nov. 5, 2009, which is incorporated herein by reference in its entirety.

BACKGROUND

In semiconductor fabrication and other fields, it is often necessary or desirable to image subsurface objects. For example, when a semiconductor chip is constructed according to "flip-chip" mounting techniques, component structures on the chip are obscured by the substrate. Various semiconductor fabrication and testing techniques require high-contrast imaging of components. Some examples of these techniques include Laser Assisted Chemical Etching, Focused Ion Beam, and others. Imaging through common substrate materials, such as silicon, is possible, although, difficulties exist.

One method of imaging through substrate material is conventional bright field microscopy. According to bright field microscopy, illumination is provided in a direction normal to the substrate surface. An image is captured with a camera or other imaging device also oriented normal to the substrate surface. While this technique can be relatively inexpensive, the resolution of the resulting images is often disappointing. This is, at least in part, because backscatter off of the substrate is directed back towards, and captured by, the objective lens of the imaging device. This has the effect of blurring and washing out the resulting image. It is known to enhance the resolution of bright field microscopy by applying an anti-reflective coating to the substrate. This method, however, is expensive and requires that the target semiconductor chip be subjected to one or more additional processing steps. It is also known to use laser scanning confocal microscopy to achieve higher resolution images through semiconductor substrates. Although laser scanning confocal microscopy does produce good results, the equipment for implementing it is extremely expensive, limiting its practical usefulness.

SUMMARY

In one general aspect, embodiments of the present invention are directed to systems and methods of imaging subsurface features of objects such as, for example, semiconductor devices. An illumination source may be directed towards a surface of an object comprising subsurface features, wherein the illumination from the source is directed at a first angle relative to the normal of the surface. The object may have a portion between the subsurface features and the surface, the portion having an index of refraction that is greater than the index of refraction of a surrounding medium that surrounds the object. An imaging device may be placed with an objective lens oriented substantially normal to the surface. The first angle may be larger than an acceptance angle of the objective lens. In some embodiments, multiple illumination beams may be generated by one or more illumination sources. The beams may be rotated relative to one another about the normal of the surface. Also, in some embodiments, multiple images may be taken with the objective of the imaging device at different positions rotated off of the normal. The multiple images may be combined to generate a composite image.

FIGURES

Various embodiments of the present invention are described here by way of example in conjunction with the following figures, wherein:

FIG. 7 illustrates one embodiment of the object of FIG. 1 showing two subsurface features and the ray reflections there from.

Figure 8:
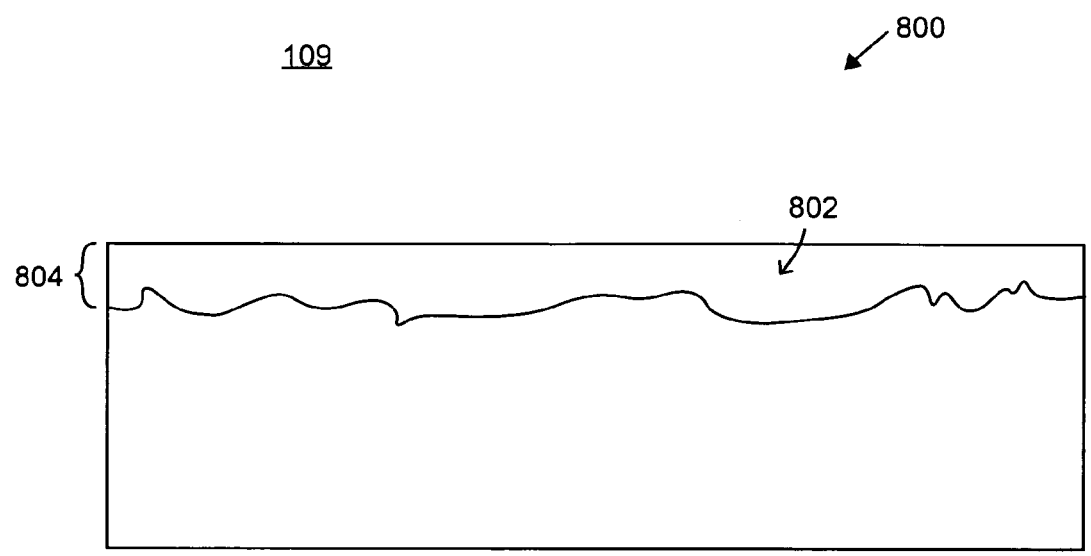

FIG. 8 a cross-sectional view of one embodiment of another object having surface features that may be observed utilizing the side addressed illumination techniques described herein.

Figure 2:
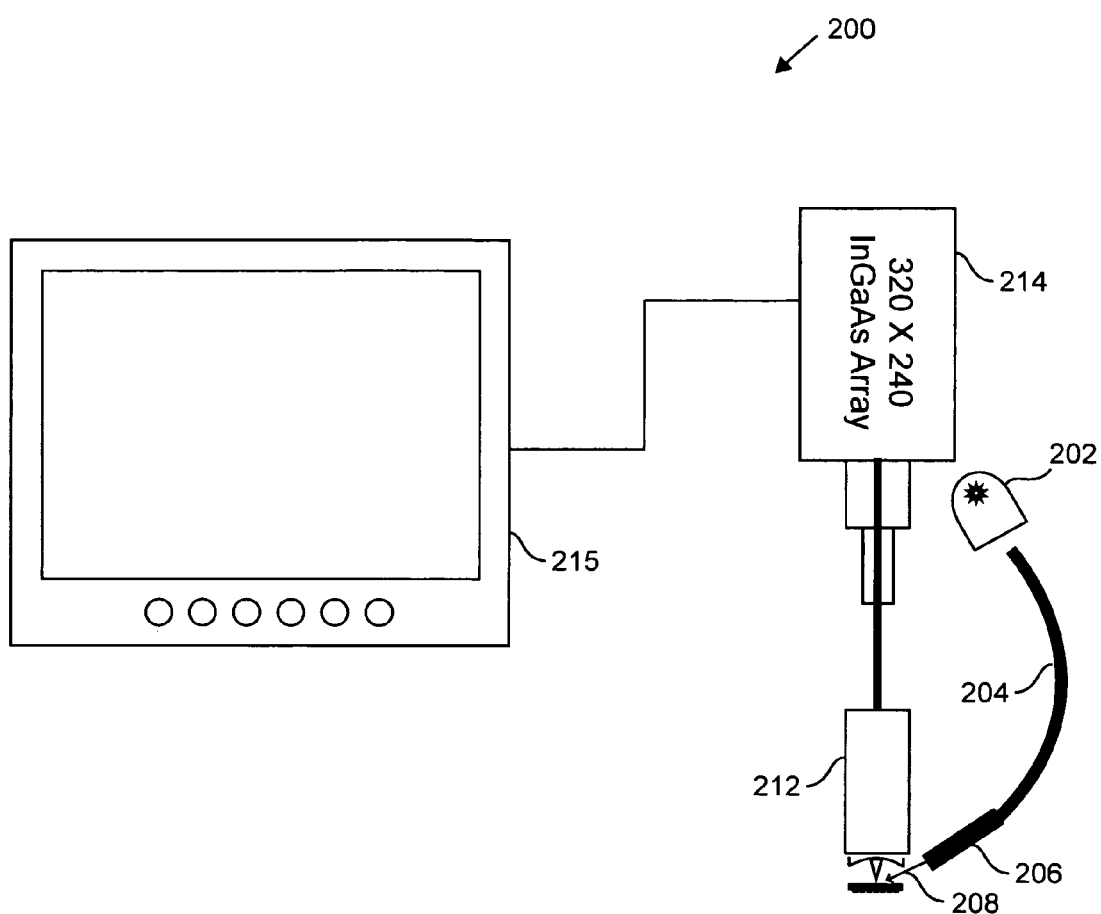
FIG. 2 illustrates one embodiment of a system for side-addressed imaging.
Figure 9:
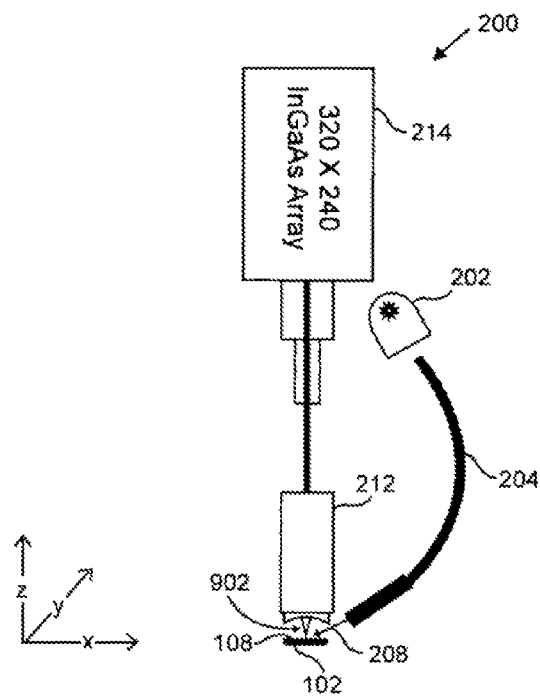

FIG. 9 shows one embodiment of the system of FIG. 2 including the imaging device, the object, the illumination source, and illumination directing elements such as, for example, the fiber optic bundle and collimating lens of FIG. 2.

Figure 10:
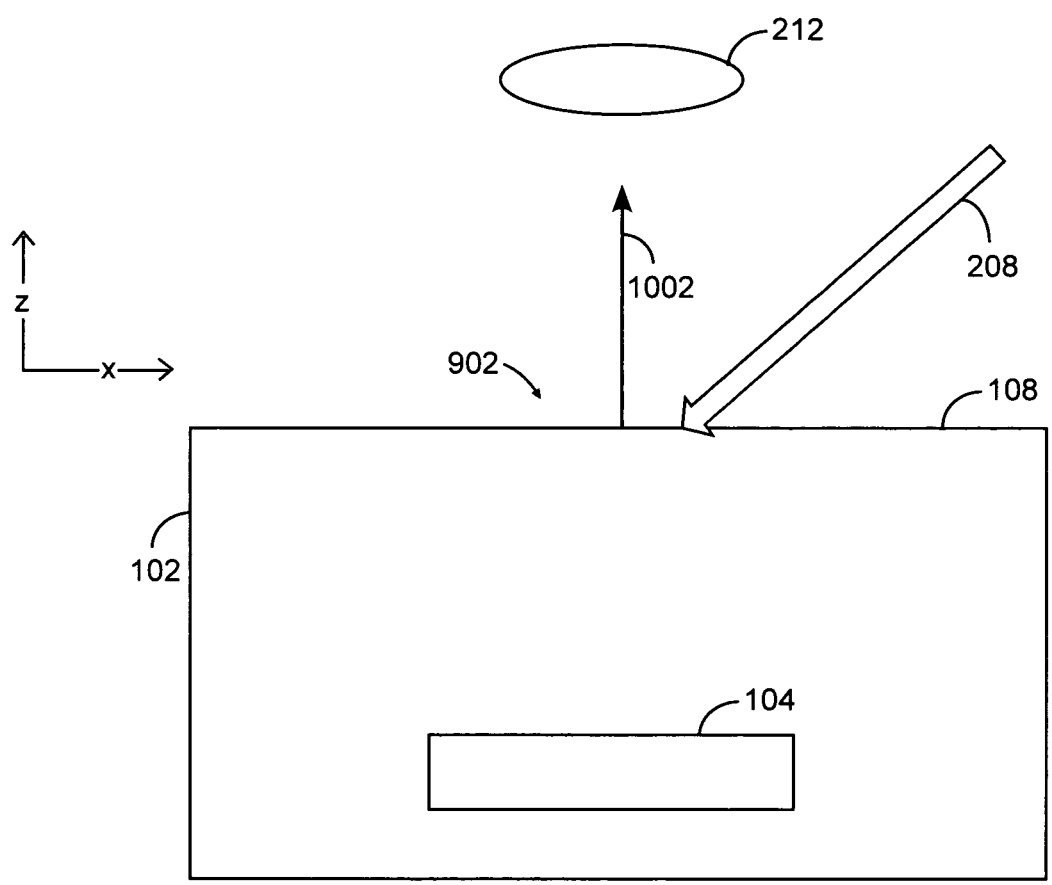

FIG. 10 illustrates a closer view of the object as illustrated in FIG. 9.

Figure 11:
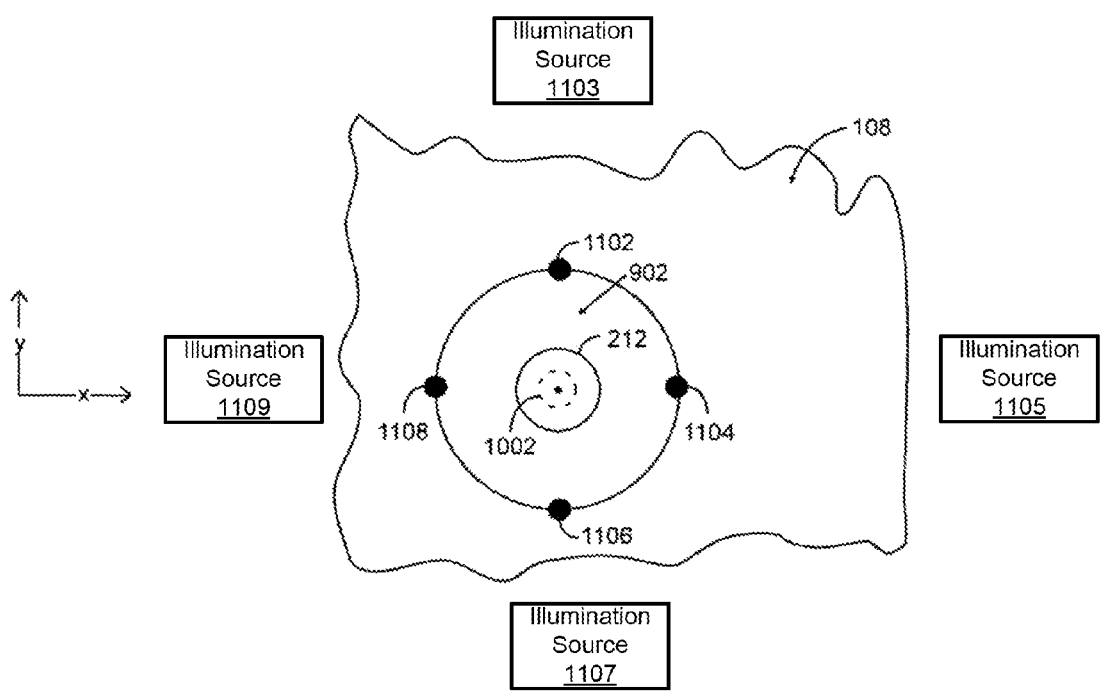

FIG. 11 illustrates a top view of the surface of the object of FIG. 10 showing four different illumination beams.

Figure 12:
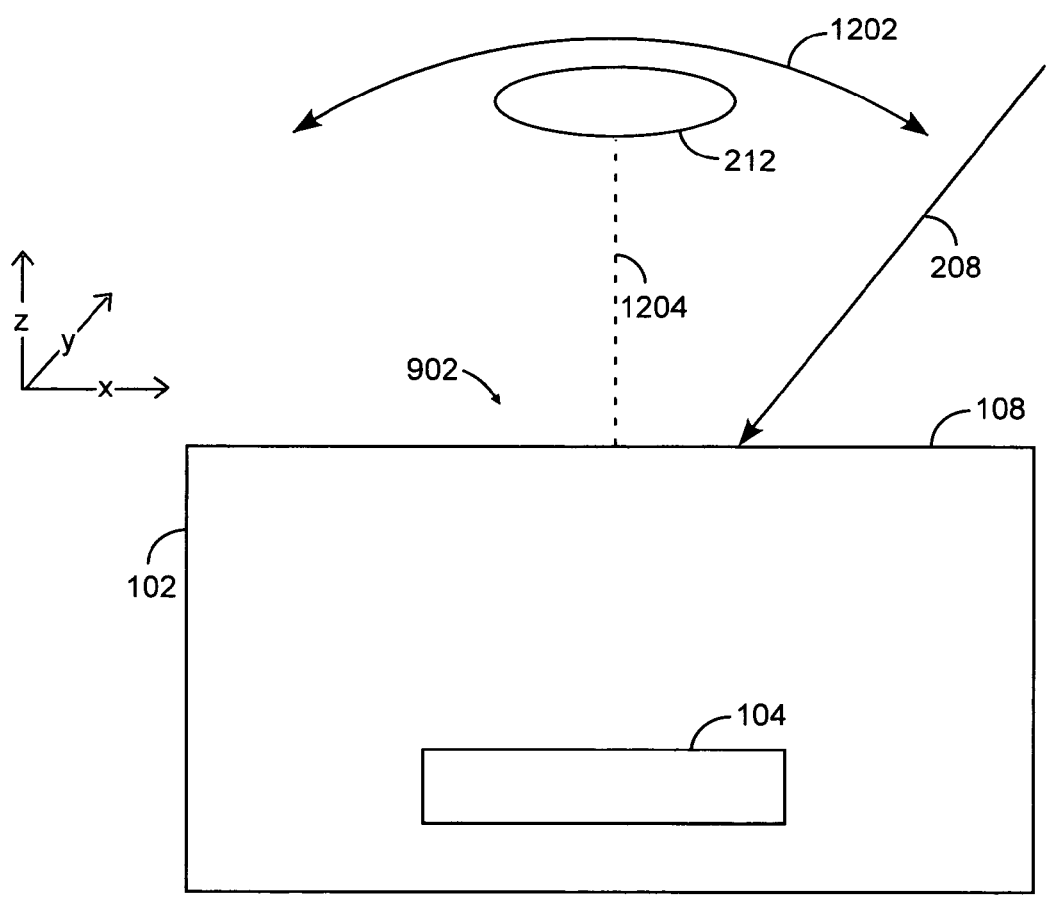

FIG. 12 illustrates one embodiment of the surface and objective illustrating how the objective may be tilted.

Figure 13:
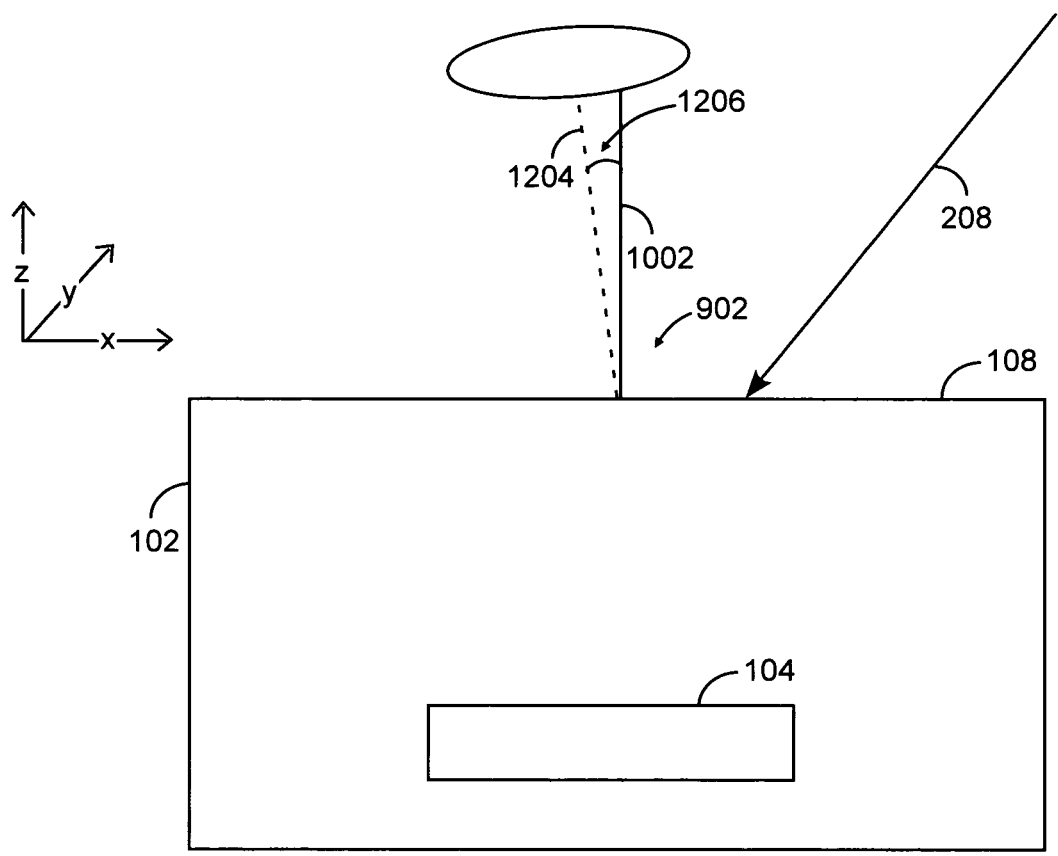

FIG. 13 illustrates one embodiment of the surface and objective with the objective tilted off of the normal by an angle.

DESCRIPTION

Various embodiments are directed to systems and methods for imaging subsurface features including, for example, semiconductor components viewed through the backside of a substrate (e.g., "backside imaging"). An illumination source may be side-addressed, or oriented at an angle relative to the normal of the surface to be imaged. An imaging device comprising an objective lens or objective may be positioned with a field of view directed substantially normal to the surface. The side-addressed position of the illumination source may provide increased image resolution in at least two ways. First, specular reflection or back-scatter off of the surface may be directed substantially outside of the acceptance angle of the objective lens. Second, when the surface over the features to be imaged has a relatively high index of refraction, refraction at the interface between the surface and the surrounding medium (e.g., air) may create a spatial filtering effect that further enhances the captured image.

According to various embodiments, it may be desirable to modify the direction of illumination and/or the perspective of the objective. This may result in images with better contrast, which may allow images to better capture feature details. In some embodiments, the surface of the object may be illuminated from multiple directions. For example, multiple side-addressed illumination beams may be directed to an image location on the surface. The illumination beams may be rotated about a normal of the surface. The separation between each of the respective illumination beams may be expressed as an angle about the surface normal. The illumination beams may be provided by a single illumination source that is rotated about the surface normal, or by multiple illumination sources placed at different positions. Also, the illumination beams may be provided simultaneously, serially, or some combination thereof. When the illumination beams are not provided simultaneously, a separate image may be captured for each illumination beam or combination of illumination beams activated at a given time. The resulting images may be combined according to any suitable algorithm to form a composite image. Utilizing multiple illumination beams may generate more uniform lighting conditions while maintaining the spatial filtering advantage described above.

In addition, or as an alternative to, using multiple illumination beams, some embodiments may further increase image resolution by tilting the direction of the objective away from the surface normal. For example, a first image may be captured with the objective tilted off of the surface normal by a first angle. A second image may be captured with the objective tilted off of the surface normal by a second angle. The two images may be combined, forming a composite image. According to various embodiments, the direction of the objective at the first angle, the direction of the objective at the second angle, and at least one illumination beam may be coplanar.

Figure 1:
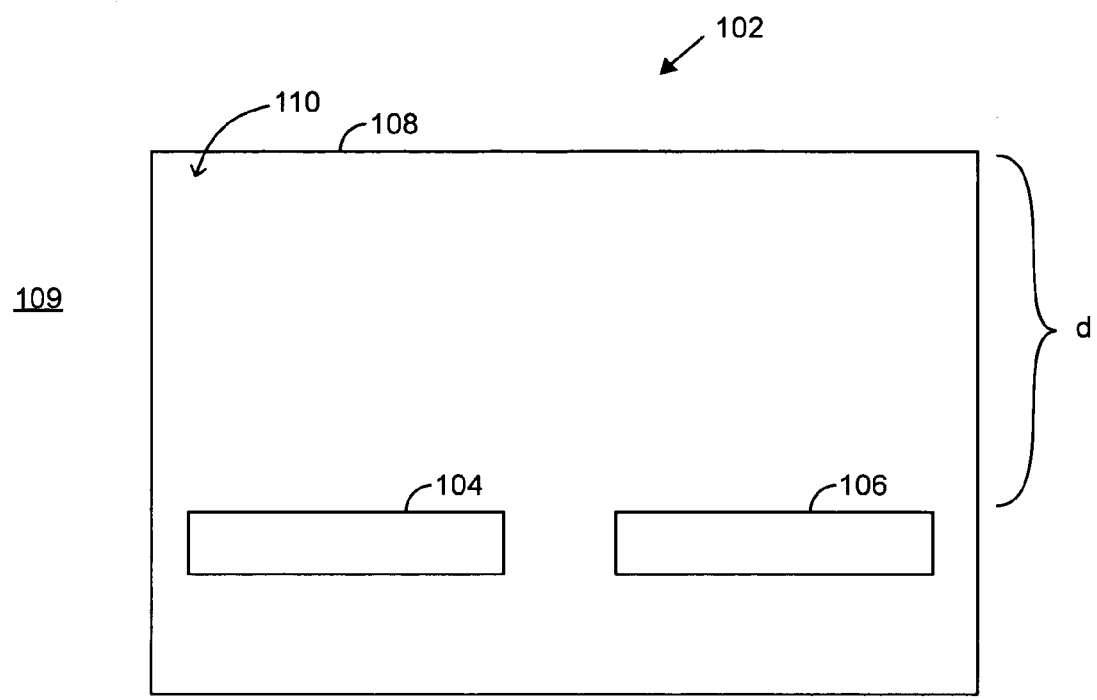
FIG. 1 illustrates a cross-sectional view of one embodiment of an object having subsurface features that may be imaged utilizing the side-addressed illumination techniques described herein.

FIG. 1 illustrates a cross-sectional view of one embodiment of an object 102 having an outer surface 108 and sub-surface features 104, 106 that may be imaged utilizing the side-addressed illumination techniques described herein. The material 110 of the object 102 between the subsurface features 104, 106 and the surface 108 may have an index of refraction at the imaging wavelength range that is greater than that of the surrounding medium 109, which may be air. The techniques and apparatuses described herein may be used to image subsurface features in many contexts. In various embodiments, however, the object 102 may comprise a semiconductor substrate and the features 104, 106 may be components such as transistors, diodes, resistors, metallization lines and/or other components formed from or on the substrate of the object 102. In this case, the imaging wavelength range may comprise some or all of the near infrared range, which is transparent in silicon. The ratio of the indices of refraction of the material 110 over the surrounding medium 109 (e.g. air) may be approximately 3.5.

It will be appreciated that, when the object 102 is a semiconductor device, the material 110 may be any suitable semiconductor material including, for example, silicon, gallium arsenide (GaAs), silicon carbide (SiC), and/or diamond. In some embodiments, the object 102 may be mounted in a flip-chip manner. Accordingly, the features 104, 106 may be visible through the remainder of the object 102 (e.g., the substrate). As viewed through the material 110, the features 104, 106 may be below the surface of the object 102 by any suitable distance d that permits transmission of illumination from an illumination source and reformation of an image by the objective or the objective lens of an imaging device (see FIG. 2). In some embodiments, the distance d may be 700 microns.

FIG. 2 illustrates one embodiment of a system 200 for side-addressed imaging. The system 200 includes an illumination source 202 optically coupled to a fiber optic bundle 204 (e.g., made of quartz or other suitable material) and a collimating lens 206. According to various embodiments, the source 202 may comprise a tungsten halogen lamp with a gold-plated reflector. It will be appreciated that suitable systems may omit various components such as the fiber optic bundle 204 and collimating lens and/or incorporate some or all of these components into the illumination source 202 itself. Light emitted by the source 202 may be incident on, and may traverse, the fiber optic bundle 204 and collimating lens 206 resulting in a beam 208 incident on the object 102 at an angle offset from the surface normal. Although the source 202 is illustrated as emitting a collimated beam, it will be appreciated that an uncollimated source may be used as well. An objective lens or objective 212 may be positioned approximately along a normal of the object 102 and may direct reflected portions of the beam 208 towards an imaging device 214. The objective 212 may comprise a lens or combination of lenses and/or apertures. The lens or lenses of the objective 212 may comprise a standard lens or, in various embodiments, may comprise a confocal lens for generating three dimensional images. According to various embodiments, the objective 212 may comprise a 1× relay optic and a an NIR 50× long working distance objective, available from MITUTOYO.

The imaging device 214 may comprise any suitable camera or other imaging element capable of sensing the imaging wavelength range. For example, as shown, the imaging device 214 may comprise a 320×240 Indium Gallium Arsenide (InGaAs) array, such as a GOODRICH SU320 sensor with 25 µm pixel pitch. The combination of the MITUTOYO NIR 50× objective 212 and the GOODRICH SU320 sensor may yield a field-of-view of 300 µm×200 µm. It will be appreciated, however, that different sensor sizes and objective components may be used to generate any suitable field of view. The imaging device 214 may capture an image and display it on a monitor 215 or similar visual display device. In addition to, or instead of, displaying the image on the monitor 215, the imaging device 214 may store captured images at a computer readable medium (not shown), such as read only memory (ROM), random access memory (RAM), a hard drive, a flash drive or other data storage device.

According to various embodiments the system 200 may utilize an imaging wavelength or wavelength range that is transparent, or near-transparent, relative to the material 110. For example, when backside imaging is performed through a silicon substrate, the imaging wavelength range may be selected to include wavelengths greater than about 1100 nm. The imaging wavelength range may be implemented in any suitable way. For example, the source 202 may be a broadband source and one or more optical filters may be positioned in the optical path between the source 202 and the imaging device 214. Also, for example, the source 202 may be a narrow-band source that emits only radiation in the imaging wavelength range. In addition to, or instead of these variations, the imaging device 214 may be a narrow band device that is sensitive only to radiation in the imaging wavelength range (e.g., an InGaAs imaging device 214 may be selected with a sensitivity between 900 nm and 1700 nm). In some embodiments, the object 102 may serve as an optical filter. For example, when the object 102 is a silicon substrate and the illumination source 202 is a broadband source, the silicon substrate may tend to absorb all wavelengths other than the near-infrared wavelengths, which are reflected and refracted as described herein.

Figure 3:
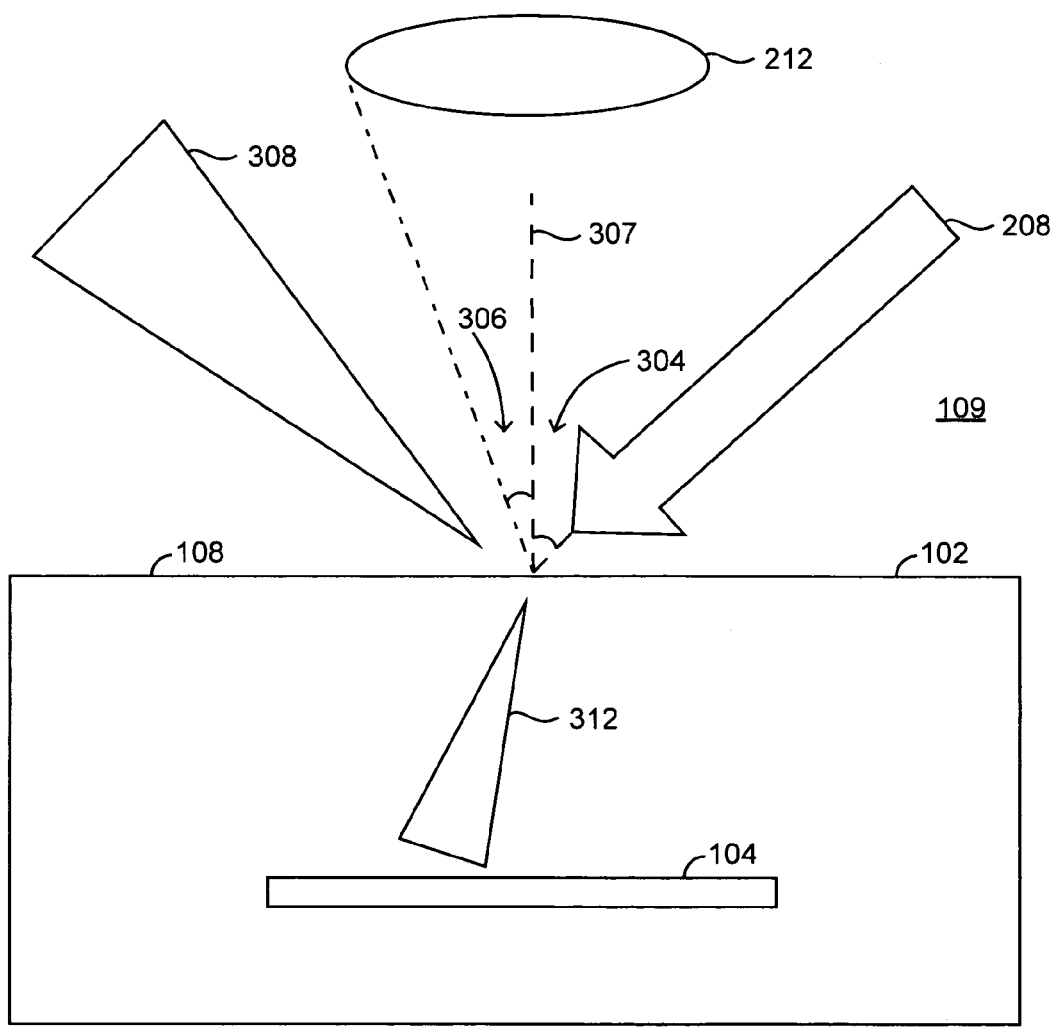
FIG. 3 illustrates one embodiment of the object of FIG. 1 illuminated by an illumination beam.

FIG. 3 illustrates one embodiment of the object 102 showing subsurface feature 104. The incident beam 208 is incident on the object 102 at an angle 304 relative to the surface normal 307. The angle 304 may be set based on the position and orientation of the illumination source 202. The angle 304 may be selected such that specular reflection of the beam 208 off of the object 102 falls outside of an acceptance angle of the objective 212. For example, the angle 304 may be at least equal to the acceptance angle 306 of the objective 212 and less than 90°. It will be appreciated that as the angle 304 increases, the intensity of the light source 202 may also need to be increased to compensate for increasing portions of the illumination beam 208 being reflected off of the object 102 out of the view of the objective 212.

In practice, reflection from the object 102 may not be perfectly specular (e.g., the surface 108 may not be perfectly smooth). Accordingly, the beam 208 may scatter off of the object 102 at a range of angles represented by cone 308. To compensate for this effect, the angle 304 may be selected to be slightly larger than the acceptance angle of the objective 212 such that the actual reflection of the beam 208 off of the object 102 falls substantially outside of the acceptance angle 306 of the objective 212. In this way, the image noise due to surface reflection may be minimized. In one example embodiment where the object 102 is a silicon substrate, the angle 304 may be 45°.

A portion of the beam 208 may be transmitted through the interface between the surrounding medium 109 (e.g., air) and the object 102. Due to the differing indices of refraction between the surrounding medium 109 and the material 110, the resulting light will be refracted towards the normal direction. Also, because the surface 108 of the object 102 may not be perfectly smooth, the refracted portion of the beam 208 may begin to spread, as represented by cone 312. The refracted portion 312 may be incident on and illuminate the feature 104 for imaging.

Figure 4:
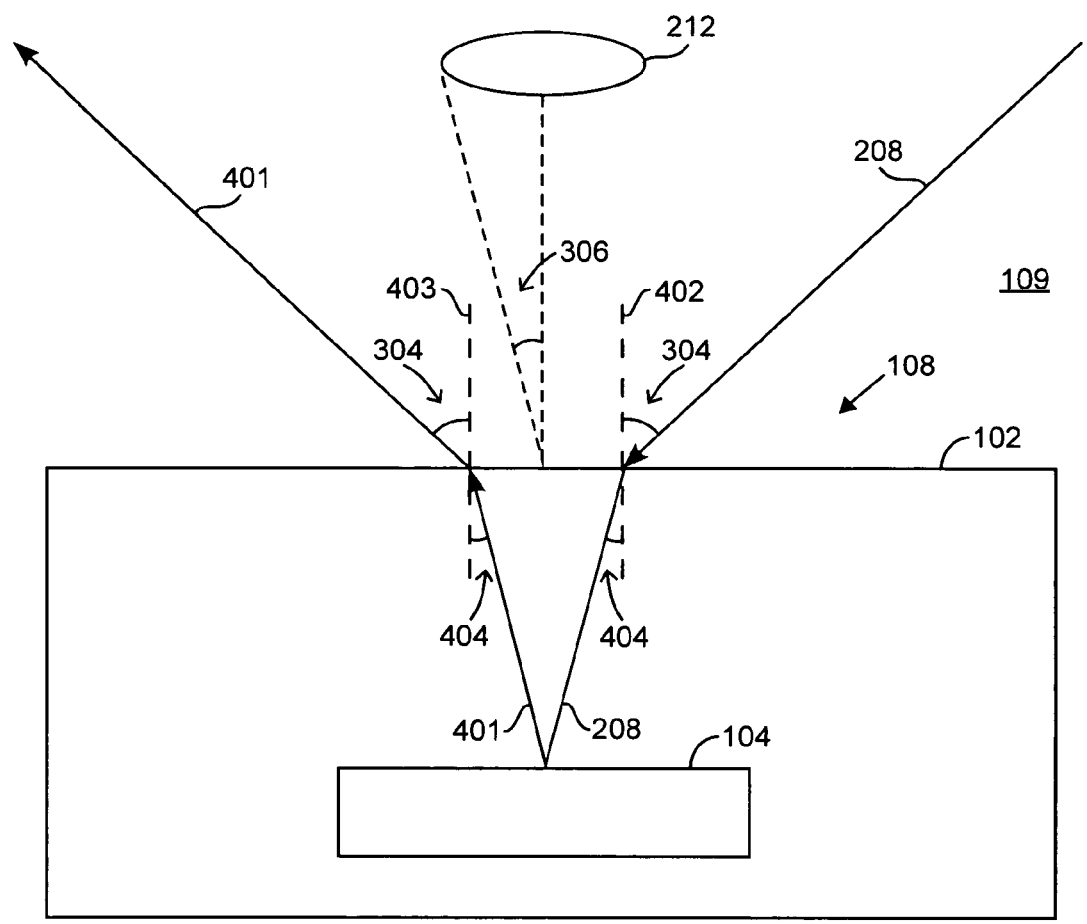
FIG. 4 illustrates one embodiment of the object of FIG. 1 illuminated by the beam oriented at an angle relative to normal of the surface of the object.

FIG. 4 illustrates one embodiment of the object 102 illuminated by the beam 208 oriented at the angle 304 relative to normal of the surface of the object 102 (represented by normal dashed lines 402, 403). At the interface between the object 102 and the surrounding medium 109, the beam 208 may be refracted such that its angle relative to the normal 402 is shown by 404. When the surrounding medium 109 is air (index of refraction ~1), the object 102 is a silicon substrate (index of refraction ~3.5) and the angle 304 is about 45°, given Snell's law, the angle 404 may be about 11.6°. After entering the object 102, the incident beam 208 may reflect off of the feature 104, resulting in a reflected beam 401. The reflected beam 401 may be incident on the surface 108 between the object 102 and the surrounding medium 109 at the angle 404 relative to the normal 403. At the surface 108, the reflected beam 401 may be refracted to the angle 304 relative to the normal 403.

Figure 5:
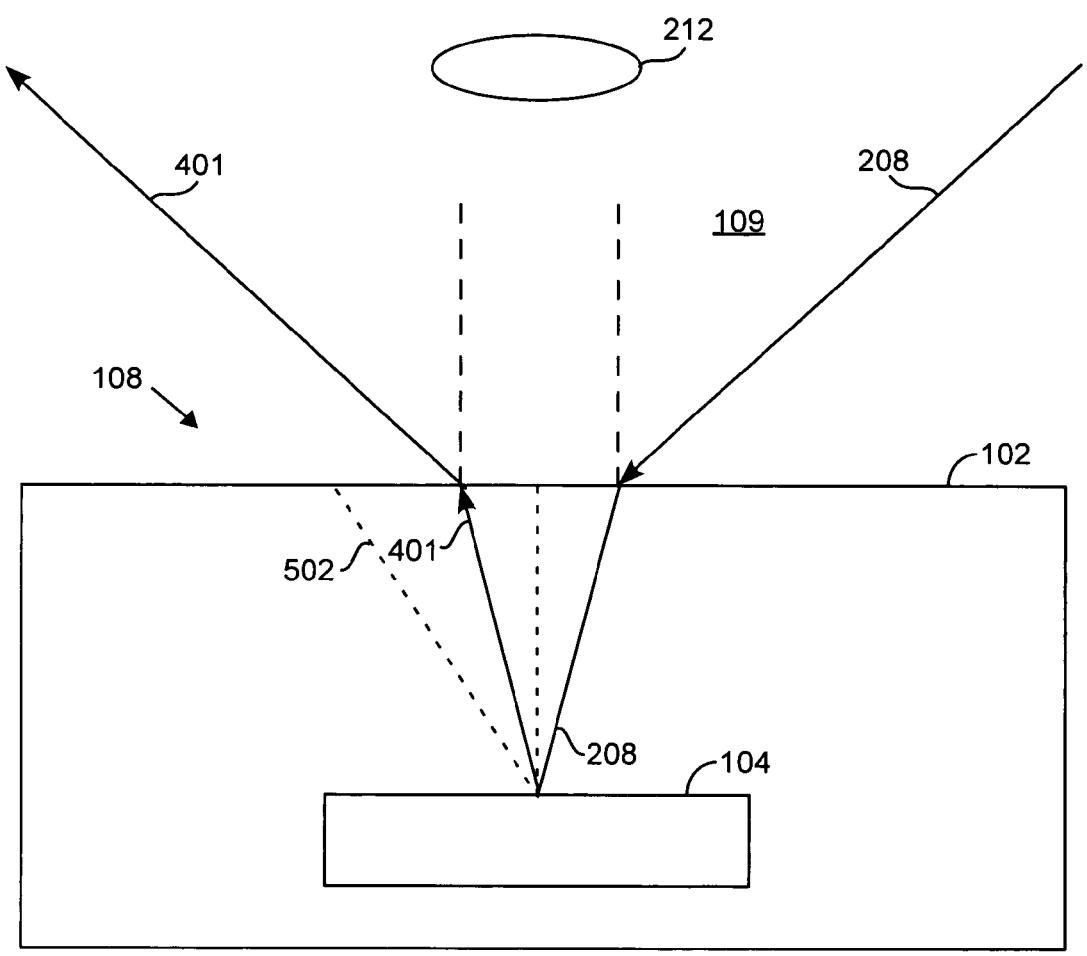
FIG. 5 illustrates one embodiment of the object of FIG. 1 showing a beam reflected off of the surface of a feature of the object over a range of angles.

It can be seen that, as illustrated in FIG. 4, the reflected beam 401 is not incident on the objective 212 within its acceptance angle 306. At least two factors, however, allow portions of the beam 401 to be incident on the objective 212. First, as illustrated in FIG. 3, roughness on the surface 108 of the object 102 may cause the incident beam 208 to actually be incident on the feature 104 over a range of angles, represented by cone 312 shown in FIG. 3. Further, surface roughness of the feature 104 may cause the reflected beam 401 to be scattered over a range 502 of angles, including angles that allow a portion of the reflected beam 401 to be incident on the objective 212 within its acceptance angle (see FIG. 5). It will be appreciated that portions of the beam 401 follow paths similar to those shown in FIG. 4 and, therefore, such portions are not incident on the objective 212. Because a portion of the reflected beam 401 is lost, it may be desirable to choose an illumination source 202 having an intensity relatively greater than what would be used for a similar bright field imaging set-up. For example, in various embodiments, the intensity of the illumination source 202 may be an order of magnitude larger than that used for a similar bright field imaging set-up.

Figure 6:
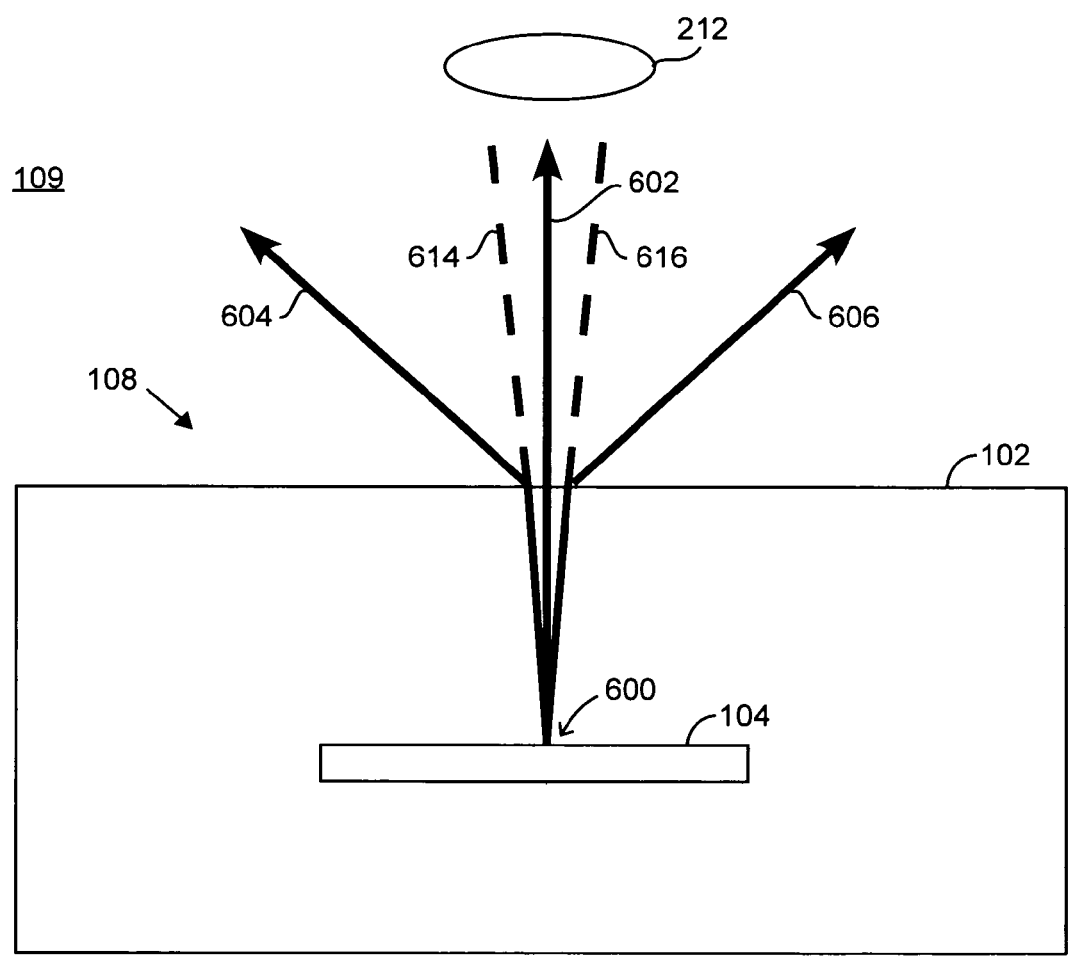
FIG. 6 illustrates one embodiment of the object and feature shown in FIG. 1 showing rays reflected by a point on the feature.

According to various embodiments, refraction at the interface between the surface 108 and the surrounding medium 109 may serve as a spatial filter, increasing the resolution of the image captured by the objective 212 by minimizing the spatial distribution of beams captured from each point of the feature 104. This effect, which can be thought of as an inverse of the Snell's window effect observed under water, is illustrated in FIG. 6. FIG. 6 shows one embodiment of the object 102 and feature 104 including rays 602, 604, 606 reflected by a point 600 on the feature 104. The ray 602 is incident on the surface/surrounding medium 109 interface at an angle within the acceptance range of the objective 212. Accordingly, the ray 602 is received by the objective 212 and transmitted to the imaging device 214 (see FIG. 2). The rays 604 and 606, in contrast, are outside of the acceptance range. As shown by un-refracted paths 614, 616, the rays 604, 606 would ordinarily be incident on objective 212 within its acceptance angle. Because of refraction, however, the rays 604, 606 are bent outside of the acceptance angle of the objective 212. As a result, the minimum spacing between subsurface objects 104 and 106 that can be resolved is based on the wavelength of the incident light 208 divided by the index of refraction of the substrate material 102, thus improving image resolution.

Figure 7:
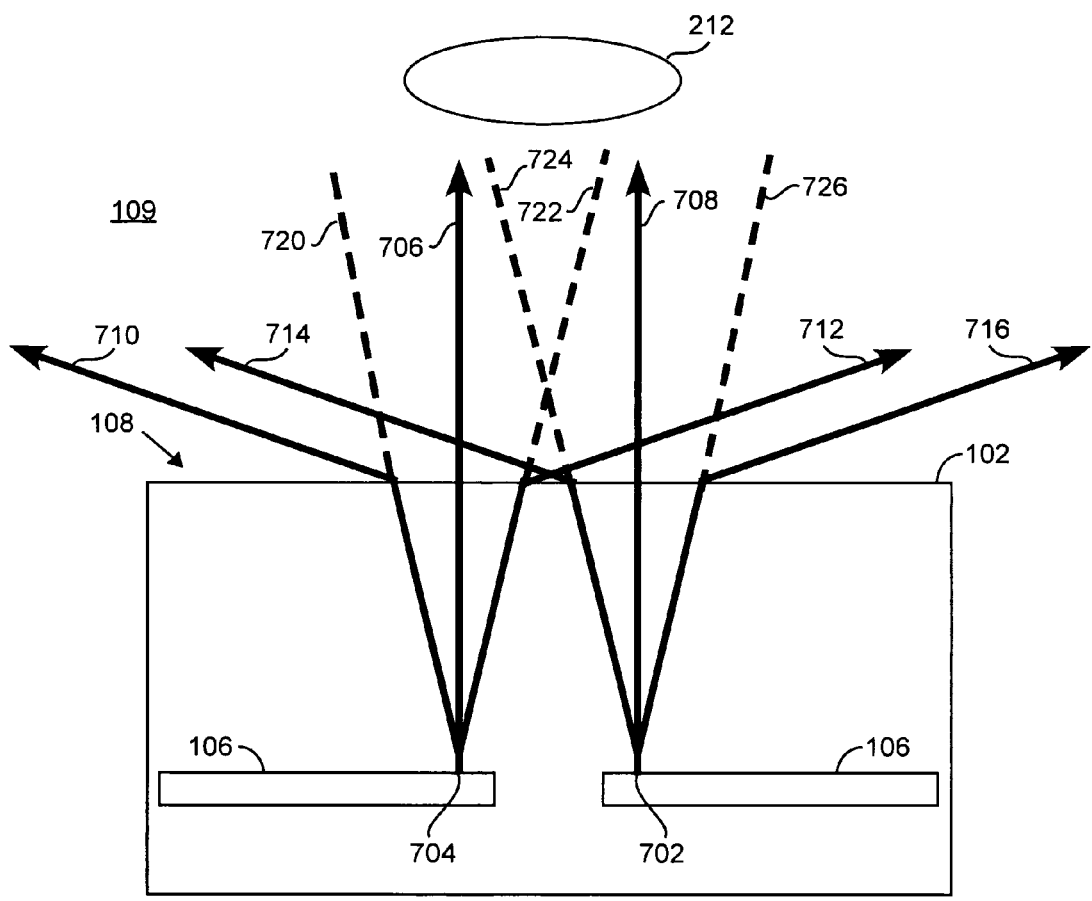

The utility of the spatial filtering effect is demonstrated by FIG. 7, which shows one embodiment of the object 102 showing both of the subsurface features 104, 106. Rays 706, 710 and 712 are reflected off of a point 704 on feature 104. Rays 708, 714 and 716 are reflected off of a point 702 on feature 106. As illustrated, rays 706 and 708 are within the acceptance range and, therefore, are incident on the objective 212. Rays 710, 714, 712 and 716, after refraction at the interface between the object 102 and the surrounding medium 109, are outside of the acceptance range and, therefore, are not incident on the objective 212. Dashed lines 720, 724, 722, 726 indicate the paths of the respective rays 710, 714, 712 absent refraction at the object 102/surrounding medium 109 interface. It will be appreciated that, but for the refraction, ray 714 from point 702 would overlap ray 706 from point 704. This would result in fuzziness and lack of clarity in the resulting image (e.g., in the image, the border between feature 104 and feature 106 would be blurred). As shown, however, the refraction between the object 102 and the surrounding medium 109 minimizes beam overlap from nearby points, thus improving image quality.

Also, for example, the apparatuses and methods described herein may be used to image features on the surface of an object by providing a temporary or permanent layer of high refractive index material over the surface prior to imaging. For example, FIG. 8 illustrates a cross-sectional view of one embodiment of another object 800 having surface features 802. The surface features 802 may be imaged by providing a layer 804 of material having a high refractive index at the imaging wavelength range. The layer 804 may be deposited onto the object 800 using any suitable deposition technique. According to various embodiments, the layer 206 may be a fluid, such as an optical coupling fluid, that may be applied to the object 800 in any suitable manner. The layer 206 may be permanent or removable.

FIGS. 9 and 10 illustrate one embodiment of the system 200 configured to provide illumination from multiple angles. For example, FIG. 9 shows one embodiment of the system 200 including the imaging device 214, the illumination source 202, and illumination directing elements such as, for example, the fiber optic bundle 204 and collimating lens 206. Illumination beam 208 is shown incident on an imaging region 902 of the surface 108 of the object 102. Directions in FIG. 9 may be indicated by the x, y and z axes shown. For example, the surface 108 may be in the x-y plane. The z-direction may be normal to the surface 108. FIG. 10 illustrates a closer view of the object 102 as illustrated in FIG. 9. A surface normal 1002 is illustrated normal to the surface 108 in the direction of the z-axis.

FIG. 11 illustrates a top view of the surface 108 showing four example illumination beams 1102, 1104, 1106, 1108. Each of the illumination beams 1102, 1104, 1106, 1108 may be directed to the imaging location 902 at an angle relative to the normal 1002. In some embodiments, all of the illumination beams may be positioned at the same angle relative to the normal 1002. In other embodiments, different illumination beams 1102, 1104, 1106, 1108 may have different angles relative to the normal 1002. As illustrated, each of the illumination beams 1102, 1104, 1106, 1108 is rotated about the normal in the x-y plane at various angles relative to one another. For example, the illumination beams 1104 and 1108 may be rotated from the beam 1102 by +90° and −90°, respectively. The beam 1106 may be similarly rotated from the beam 1102 by 180°.

It will be appreciated that the various illumination beams 1102, 1104, 1106, 1108 may be generated by a single illumination source 202, which may be rotated or otherwise directed to the position of each beam 1102, 1104, 1106, 1108. In some embodiments, multiple illumination sources may be used. For example, each beam 1102, 1104, 1106, 1108 may be generated by a separate illumination source (1103, 1105, 1107, 1109). Also, although four illumination beams 1102, 1104, 1106, 1108 are shown, it will be appreciated that beams may be omitted or added. For example, in some embodiments, it may be desirable to have three beams. A first beam may be considered to be positioned at 0°. A second beam may be rotated about the normal 1002 by +45°, and a third beam may be rotated about the normal 1002 by −45°.

According to various embodiments, all of the beams 1102, 1104, 1106 may be illuminated at the same time. In this case, a single image of the imaging region 902 may be captured with all of the illumination beams 1102, 1104, 1106, 1108 active. In some embodiments, however, less than all of the beams 1102, 1104, 1106, 1108 may be illuminated at the same time. For example, in some embodiments, the beams 1102, 1104, 1106, 1108 may be illuminated separately or in a combination of less than all of the beams 1102, 1104, 1106, 1108. A separate image may be captured while each beam or combination of beams 1102, 1104, 1106 is illuminated. The resulting images may be composted or otherwise combined to form a composite image.

According to various embodiments, the number and orientations of the illumination beam or beams in the x-y plane may be determined based on the orientation of the surface 108 and any sub-surface features 104. For example, illuminating a surface 108 in a direction parallel to and in a direction perpendicular to sub-surface features 104 may, in some embodiments, provide increased resolution. When the object 102 is a semiconductor chip, the sub-surface features 104 may be arranged in a grid-like Manhattan-style configuration. Accordingly, at least two illumination beams may be utilized with the illumination beams aligned with the grid of the sub-surface features 104 and separated from one another about the normal 1002 by 45°. When X-architecture chips or other non-Manhattan-style objects are imaged, different illumination beam directions may be selected to illuminate the parallel and perpendicular directions of major sub-surface features 104.

In some embodiments, the objective 212 may be tilted relative to the surface normal 1002 to capture images of the imaging region 902 from multiple directions. The captured images may then be composted or otherwise combined to form a composite image. FIG. 12 illustrates one embodiment of the surface 108 and objective 212 showing an arrow 1202 along which the direction 1204 of the objective 212 may be tilted. According to various embodiments, and as indicated by the arrow 1202, the direction 1204 of the objective 212 may be tilted off of the normal 1002 while remaining in the same plane as the illumination beam 208. (Note that in FIG. 12, the normal 1002 and the direction 1204 of the objective 1204 are the same.) In the example shown in FIG. 12, the illumination beam 208 and objective direction 1204 are shown in the x-z plane. Accordingly, in the illustrated example, the direction 1204 objective 212 may be rotated off of the normal 1002 in the x-z plane. It will be appreciated that the illumination beam 208, and therefore the direction of objective 212 tile, need not always be in the x-z plane (e.g., as illustrated in FIG. 11).

The amount of objective 212 tilt may be expressed as an angle between the direction 1204 of the objective 212 and the normal 1002. FIG. 13 illustrates one embodiment of the surface 108 and objective 212 with the objective 212 tilted off of the normal 1002 by an angle 1206. It will be appreciated that the number of images and the objective 212 positions from which the images are captured may vary. For example, according to various embodiments, a first image may be captured with the angle 1206 equal to +10° and a second image may be captured with the angle 1206 equal to −10°.

In some embodiments, multiple illumination beams (as illustrated by FIGS. 9-11) may be utilized in conjunction with multiple objective positions (as illustrated by FIGS. 12-13). For example, when there are multiple illumination beams, a series of images with the objective 212 at different tilt levels, may be captured in each plane containing at least one illumination beam.

In embodiments where multiple images are composted to form a composite image, any suitable image combining algorithms may be used. For example, when two images are combined, stereographic techniques may be used. According to stereographic techniques, a first image from a first angle may be colored with a first hue (e.g. blue) while a second image from a second angle may be colored with a second hue (e.g., green). The two colored images may be superimposed on one another, resulting in a three-dimensional image that may be viewed with appropriate optics (e.g., filters matching the image hues). Stereographic techniques may be useful in situations where two images are complimentary. For example, images taken with the objective 212 tilted by the same amount in two different directions away from the normal 1002 may be complimentary. Also, for example, images taken with illumination beams in the same plane may be complimentary.

Additional image combining techniques may be used, for example, when more than two images are combined. For example, it will be appreciated that composite images may tend to wash out as more component images are combined. Any suitable technique may utilized to minimize this effect. For example, each component image may first be digitally stretched and then overlaid with one another with a given transparency factor (e.g., 50%).

Although the figures above are described in the context of backside imaging of semiconductor devices, it will be appreciated that the apparatuses and methods disclosed herein may be used in various other contexts as well. For example, the apparatuses and methods used herein may be used to image any subsurface features where the index of refraction of material between a surface of an object and subsurface features of the object is relatively greater than that of the surrounding medium 109.

It is to be understood that the figures and descriptions of the present invention have been simplified to illustrate elements that are relevant for a clear understanding of the present invention, while eliminating other elements, for purposes of clarity. Those of ordinary skill in the art will recognize that these and other elements may be desirable. However, because such elements are well known in the art and because they do not facilitate a better understanding of the present invention, a discussion of such elements is not provided herein.

In various embodiments disclosed herein, a single component may be replaced by multiple components and multiple components may be replaced by a single component to perform a given function or functions. Except where such substitution would not be operative, such substitution is within the intended scope of the embodiments.

While various embodiments have been described herein, it should be apparent that various modifications, alterations, and adaptations to those embodiments may occur to persons skilled in the art with attainment of at least some of the advantages. The disclosed embodiments are therefore intended to include all such modifications, alterations, and adaptations without departing from the scope of the embodiments as set forth herein.

We claim:

1. A method of imaging subsurface features of an object, the method comprising:
    illuminating the object with a first illumination beam directed towards an imaging location on a surface of the object at a first angle relative to a normal of the surface;
    illuminating the object with a second illumination beam directed towards the imaging location at the first angle relative to the normal of the surface, wherein the second illumination beam is rotated about the normal by a second angle relative to the first illumination beam, wherein the first and second illumination beams comprise illumination in an imaging wavelength range, wherein the object comprises subsurface features, and wherein the object comprises material positioned between the surface and the subsurface features, the material having an index of refraction that is greater than an index of refraction of a surrounding medium that at least partially surrounds the object;
    capturing reflected illumination from the surface of the object with an imaging device comprising an objective lens having an acceptance angle, wherein the first angle is greater than the acceptance angle.

2. The method of claim 1, wherein the illuminating the object with the first illumination beam and the illuminating the object with the second illumination beam are performed at the same time.

3. The method of claim 1, wherein the illuminating the object with the first illumination beam is performed at a first time and the illuminating the object with the second illumination beam is performed at a second time; and
    wherein the capturing reflected illumination comprises:
        capturing a first image of the surface at the first time; and
        capturing a second image of the surface at the second time; and
    wherein the method further comprises combining the first image and the second image to form a composite image of the imaging location.

4. The method of claim 3, wherein the second angle is 90°.

5. The method of claim 1, wherein the capturing comprises:
    capturing a first image of the imaging location with the objective directed towards the imaging location in a first direction rotated off of the normal by a first position angle; and
    capturing a second image of the imaging location with the objective directed towards the imaging location in a second direction rotated off of the normal by a second position angle.

6. A system for imaging subsurface features of an object, the system comprising:
    an imaging device sensitive to an imaging wavelength range, the imaging device comprising an objective lens;
    a first illumination source to generate a first illumination beam having an imaging wavelength range, wherein the first illumination beam is directed towards an imaging location of a surface of the object at a first angle relative to a normal of the surface, wherein the object comprises subsurface features, wherein the object comprises material between the surface and the subsurface features, wherein the material has an index of refraction that is greater than an index of refraction of a surrounding medium that at least partially surrounds the object, and wherein the first angle is greater than an acceptance angle of the objective lens of the imaging device; and
    a second illumination source, wherein the second illumination source is positioned to emit a second illumination beam rotated about the normal of the surface by a second angle.

7. The system of claim 6, wherein the second angle is 90°.

8. A method of imaging subsurface features of an object, the method comprising:
    illuminating the object with an illumination beam directed towards the imaging location at a first angle relative to the normal of the surface, wherein the illumination beam comprises illumination in an imaging wavelength range, wherein the object comprises subsurface features, and wherein the object comprises material positioned between the surface and the subsurface features, the material having an index of refraction that is greater than an index of refraction of a surrounding medium that at least partially surrounds the object;
    capturing reflected illumination from the surface of the object with an imaging device comprising an objective, wherein the objective comprises an objective lens having an acceptance angle, wherein the first angle is greater than the acceptance angle, and where the capturing comprises:
        capturing a first image of the imaging location with the objective directed towards the imaging location in a first direction rotated off of the normal by a first position angle; and
        capturing a second image of the imaging location with the objective directed towards the imaging location in a second direction rotated off of the normal by a second position angle; and
    combining the first image and the second image to form a composite image of the imaging location.

9. The method of claim 8, wherein the second position angle is 90°.

10. The method of claim 9, wherein the illumination beam, the first direction and the second direction are coplanar.

11. The method of claim 8, wherein the first position angle and the second position angle are equal.

12. The method of claim 8, wherein the first and second position angles are equal to 10°.

13. The method of claim 8, further comprising illuminating the object with a second illumination beam directed towards the imaging location at the first angle relative to the normal of the surface, wherein the second illumination beam is rotated about the normal by a second angle relative to the first illumination beam.

14. A system for imaging subsurface features of an object, the system comprising:
- an illumination source to generate an illumination beam having an imaging wavelength range, wherein the illumination beam is directed towards an imaging location of a surface of the object at a first angle relative to a normal of the surface, wherein the object comprises subsurface features, wherein the object comprises material between the surface and the subsurface features, wherein the material has an index of refraction that is greater than an index of refraction of a surrounding medium that at least partially surrounds the object, and wherein the first angle is greater than an acceptance angle of the objective lens of the imaging device; and
- an imaging device sensitive to an imaging wavelength range, the imaging device comprising an objective, wherein the objective comprises an objective lens, and wherein the imaging device is to:
  - capture a first image of the imaging location with the objective directed towards the imaging location in a first direction rotated off of the normal by a first position angle; and
  - capture a second image of the imaging location with the objective directed towards the imaging location in a second direction rotated off of the normal by a second position angle; and
- a computer device in electronic communication with the imaging device, wherein the computer device is to:
  - receive the first image and the second image; and
  - combine the first image and the second image to form a composite image of the imaging location.

15. The system of claim 14, wherein the second position angle is 90°.

16. The system of claim 15, wherein the illumination beam, the first direction and the second direction are coplanar.

17. The system of claim 14, wherein the first position angle and the second position angle are equal.

18. The system of claim 14, wherein the first and second position angles are equal to 10°.

* * * * *